United States Patent
Lüke et al.

(10) Patent No.: US 6,238,859 B1
(45) Date of Patent: May 29, 2001

(54) VIRUS PROTEIN ANTIGENS OF THE JC VIRUS

(75) Inventors: Wolfgang Lüke; Gerhard Hunsmann, both of Göttingen; Thomas Weber, Hamburg, all of (DE)

(73) Assignee: Deutsches Primatenzentrum, Gottingen (DE)

( * ) Notice: Subject to any disclaimer, the term of this patent is extended or adjusted under 35 U.S.C. 154(b) by 0 days.

(21) Appl. No.: 09/068,569

(22) PCT Filed: Nov. 22, 1996

(86) PCT No.: PCT/EP96/05177

§ 371 Date: Jul. 17, 1998

§ 102(e) Date: Jul. 17, 1998

(87) PCT Pub. No.: WO97/19174

PCT Pub. Date: May 29, 1997

(30) Foreign Application Priority Data

Nov. 22, 1995 (DE) ............................................... 195 43 553

(51) Int. Cl.[7] ............................... C12Q 1/68; C12Q 1/70; C12N 7/04; C12N 15/40; C12N 15/86
(52) U.S. Cl. ........................ 435/5; 435/69.1; 435/235.1; 435/320.1; 435/455; 435/456; 435/366; 435/348; 435/6; 435/7.1; 435/236; 530/350
(58) Field of Search ................................ 435/69.1, 235.1, 435/320.1, 455, 456, 366, 348, 5, 6, 7.1, 236; 530/350; 424/93.2, 93.6, 185.1, 186.1, 204.1, 281.1; 514/2

(56) References Cited

PUBLICATIONS

Andrea D. Branch, TIBS, vol. 23, pp. 45–50, Feb. 1998.*
Trisha Gura, Science, vol. 270, pp. 575–577, Oct. 27, 1995.*
Nature Biotechnology, vol. 15, pp. 519–524, Jun. 1997.*
W. French Anderson, Nature, vol. 392, pp. 25–30, Apr. 30, 1998.*
Ross et al., Human Gene Therapy, vol. 7, pp. 1781–1790, Sep. 10, 1996.*
Verma et al., Nature, vol. 389, pp. 239–242, Sep. 18, 1997.*
Goldman et al., J. Virol., vol. 73, No. 5, pp. 4465–4469, May 1999.*
Major et al., Clinical Microbiology Reviews, vol. 5, No. 1, pp. 49–73, Jan. 1992.*
Jon Cohen, Science, vol. 265, pp. 1371–1373, Sep. 2, 1994.*
Iida et al., Proc. Natl. Acad. Sci. USA, vol. 90, pp 5062–5065, Jun. 1993, "Origin of JC Polyomavirus variants associated with progressive multifocal leukoencephalopathy".
Weber et al., AIDS, 1994, vol. 8, No. 1, "Progressive multifocal leukoencephalopathy diagnosed by amplification of JC virus–specific DNA from cerebrospinal fluid."
International Publication No. WO 94/20137, published Sep 15, 1994.
Travis, J.E., Walker, D.L., Gardner, S.D., and Frisque, R.J. (1989), Nucleotide sequence of the human polymavirus AS virus, an antigenic of BK virus, J. Virol. 63, 901–911.
Sililaty, S.N., Berns K.L., and Aposhian, H.V. (1982), Polyoma–like particle: characterisation of the DNA encapsidated in vitro by polyoma empty capsids, J. Biol. Chem. 257, 6571–6575.
Forstova, J., Krauzewics, N., Sandig, V., Elliot, J., Plakova, Z., Strauss, M. and Griffin, B.E. (1995), Polyoma virus pseudocapsids as efficient carriers of heterologous DNA into mammalian cells, Hum. Gen. Ther. 6, 297–306.

\* cited by examiner

*Primary Examiner*—David Guzo
(74) *Attorney, Agent, or Firm*—Arent Fox Kintner Plotkin & Kahn, PLLC

(57) ABSTRACT

The invention concerns new virus-like particles composed of the VP1 protein of the JC virus, a process for their production and their use in analytical, diagnostic and therapeutic methods.

26 Claims, 5 Drawing Sheets

Fig.1

CLONING THE STRUCTURAL PROTEINS OF JCV

JCV FROM OMA586 → SVG → PCR WITH MUTATING PRIMERS

M VP1 VP2 VP3

Figure 2:
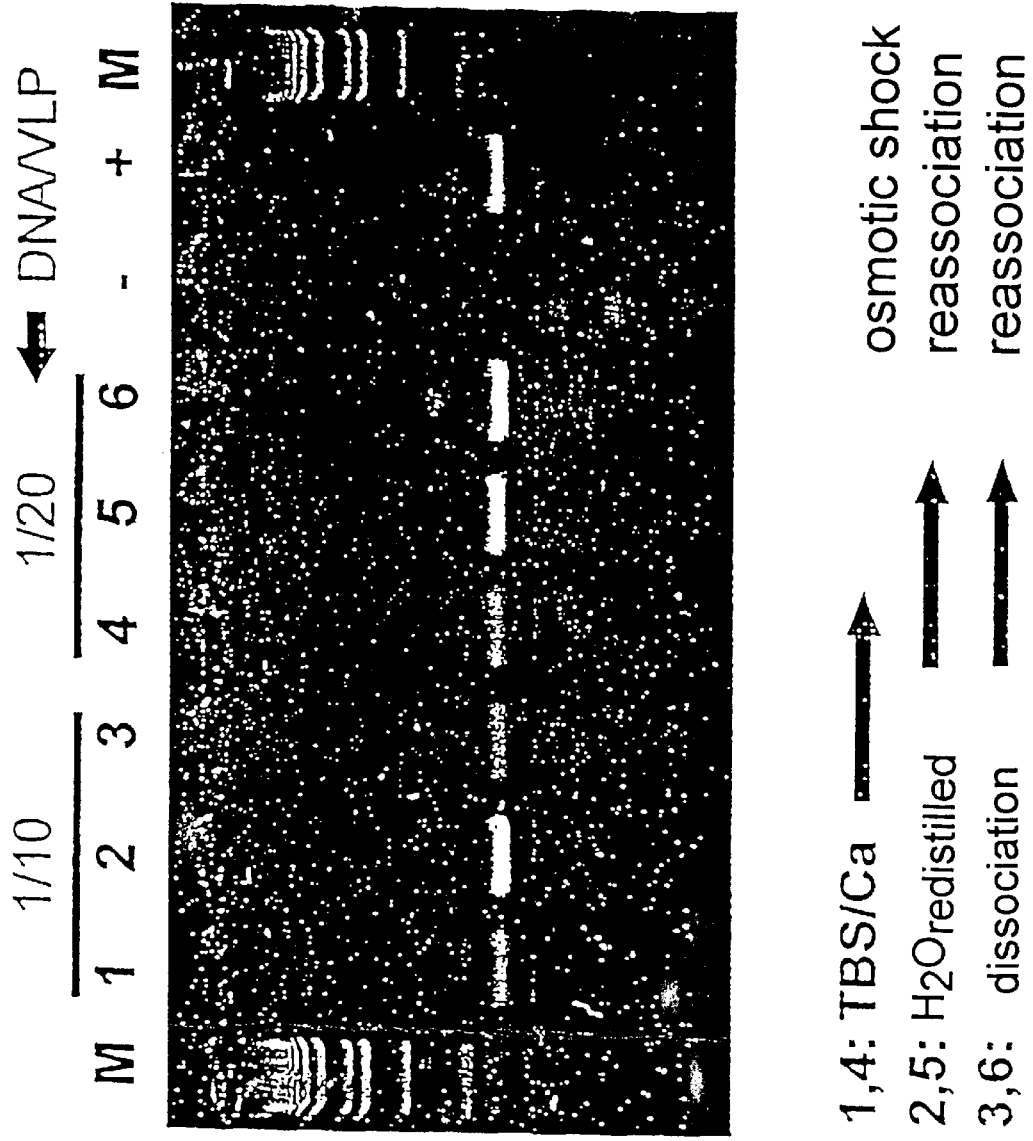

ELUTION OF THE PCR AMPLIFICATES pBlueBac
BamHI  HindIII

VP GENE
BamHI  HindIII

RESTRICTION DIGESTION AND LIGATION pBlueBac-VP
BamHI  HindIII
VP GENE

TRANSFORMATION → E.coli

PLASMID ISOLATION

HOMOLOGOUS RECOMBINATION AND TRANSFECTION

Sf158

Baculo-WT DNA

RECOMBINANT BACULOVIRUSES

SEQUENCE LISTING

<160> NUMBER OF SEQ ID NOS: 4

<210> SEQ ID NO 1
<211> LENGTH: 1121

```
<212> TYPE: DNA
<213> ORGANISM: JC virus

<400> SEQUENCE: 1
gtacgggact gcagcacctg ctcttgaagc atatgaagat ggccccaaca aaagaaaag      60 gagaaaggaa ggaccccgtg caagttccaa aacttcttat aagaggagga gtagaagttc    120
tagaagttaa aactggggtt gactcaatta cagaggtaga atgctttta actccagaaa     180 tgggtgaccc agatgagcat cttaggggtt ttagtaagtc aatatctata tcagatacat    240
ttgaaagtga ctccccaaat agggacatgc ttccttgtta cagtgtggcc agaattccac    300
tacccaatct aaatgaggat ctaacctgtg gaaatatact catgtgggag gctgtgacct    360
taaaaactga ggttataggg gtgacaagtt tgatgaatgt gcactctaat gggcaagcaa    420
ctcatgacaa tggtgcaggg aagccagtgc agggcaccag ctttcatttt ttttctgttg    480 gggggaggc tttagaatta caggggtgc ttttaatta cagaacaaag tacccagatg         540
gaacaatttt tccaaagaat gccacagtgc aatctcaagt catgaacaca gagcacaagg    600
cgtacctaga taagaacaaa gcatatcctg ttgaatgttg ggttcctgat cccaccagaa    660
atgaaaacac aagatatttt gggacactaa caggaggaga aaatgttcct ccagttcttc    720
atataacaaa cactgccaca acagtgttgc ttgatgaatt tggtgttggg ccactttgca    780
aaggtgacaa cttatacttg tcagctgttg atgtctgtgg catgtttaca aacaggtctg    840
gttcccagca gtggagagga ctctccagat attttaaggt gcagctaagg aaaaggaggg    900
ttaaaaaccc ctacccaatt tctttccttc ttactgattt aattaacaga aggactccta    960
gagttgatgg gcagcctatg tatggcatgg atgctcaagt agaggaggtt agagttttg    1020 agggaacaga ggagcttcca ggggacccag acatgatgag atacgttgac aaatatggac    1080
agttgcagac aaaaatgctg taatcaaaag ctttttattgt a                       1121

<210> SEQ ID NO 2
<211> LENGTH: 354
<212> TYPE: PRT
<213> ORGANISM: JC virus

<400> SEQUENCE: 2

Met Ala Pro Thr Lys Arg Lys Gly Glu Arg Lys Asp Pro Val Gln Val
 1               5                  10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
```

```
                        -continued
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
                340                 345                 350

Met Leu

<210> SEQ ID NO 3
<211> LENGTH: 29
<212> TYPE: DNA
<213> ORGANISM: JC virus

<400> SEQUENCE: 3
gtacgggact gcagcacctg ctcttgaag                                    29

<210> SEQ ID NO 4
<211> LENGTH: 29
<212> TYPE: DNA
<213> ORGANISM: JC virus

<400> SEQUENCE: 4
tacaataaaa gcttttgatt acagcattt                                    29
```

VIRUS PROTEIN ANTIGENS OF THE JC VIRUS

DESCRIPTION

The present invention concerns new virus-like particles and their use in analytical, diagnostic and therapeutic methods.

The JC virus (JCV) belongs to the group of human polyoma viruses. JCV can cause a sub-acute demyelinizing disease of the brain by a lytic infection of myelin-forming oligodendrocytes and an abortive infection of astrocytes. This infection, which is referred to clinically as progressive multifocal leukoencephalopathy (PML), leads to the formation of demyelinizing foci in the cerebrum cerebellum and brain stem and usually ends lethally within a few months.

With PML there is usually no significant humoral or cellular immune response to JCV which makes it difficult to diagnose the disease. Although JCV appears to be present in about 80% of the adult population, PML generally only develops in connection with a weakening of the immune system. The increasing use of immuno-suppressive drugs and the increasing number of HIV-infected patients has led to a considerable increase in PML diseases in recent years. According to current estimations a PML develops in about 2–5% of AIDS patients.

The known methods of diagnosis for detecting a PML disease essentially comprise image forming methods such as CT (computer tomography) and MRI (magnetic resonance imaging) as well as immunocytochemical methods based on biopsies or autopsies. Recently PCR detection methods have increased in importance, virus DNA amplification from cerebrospinal fluid (CSF) yielding reliable and specific results (Weber et al., J. Infect. Dis. (1994), 1138–1141 and McGuire et al., Annals of Neurology 37 (1995), 395–399).

The disadvantages of the diagnostic methods known from the state of the art are that they can only be carried out with a large amount of work and are therefore unsuitable for a reliable routine diagnosis. This also applies to PCR methods in which there is a high contamination risk that can lead to a falsification of the results. It would therefore be desirable to have available a method and reagents which allow a reliable diagnosis of PML in a more simple manner. Furthermore there is a need for an agent that can be used for the therapeutic treatment of PML diseases.

Hence the object of the invention is to provide methods and reagents with which the above-mentioned goals can be achieved and which at least partially avoids the disadvantages of the state of the art.

It was surprisingly found that the virus protein 1 (VP1) of the JC virus is an excellent agent for the immunochemical detection of JCV. Furthermore it was found that VP1 can be produced in a large yield in the form of virus-like particles (VLP) by recombinant DNA techniques.

Hence one subject matter of the invention is a virus-like particle (VLP) which is composed of several molecules of the virus protein 1 (VP1), the main structural protein of the JC virus. This VLP is in particular characterized in that it has a structure that reacts immunologically with anti-JCV antisera and is free of nucleic acids associated with JCV.

It was surprisingly found that, after purification, recombinant VP1 of JCV can associate to form virus-like particles (VLP). Such VLP have an icosahedral structure with a diameter of about 50 nm. The advantage of VLP over an individual VP1 protein is above all that the properties or/and effects of the natural virus are more exactly simulated and that a broader field of application is opened up. Further advantages over the natural virus are, in particular, increased work safety and it was surprisingly also found that the VLP has a higher immunogenicity than the purified total virus.

The VP1 of JCV is the main structural protein of the capsid envelope of JCV e.g. from wild-type strains or mutagenized strains of JCV. In a special embodiment the VLP is composed of recombinantly produced VP1. In this case the term VP1 also encompasses proteins which differ from wild-type VP1 by mutations such as substitutions, insertions or/and deletions. In order to produce recombinant VP1 one preferably uses a nucleic acid which comprises the sequence shown in SEQ ID NO.1, a sequence corresponding to this within the scope of the degeneracy of the genetic code or a sequence hybridizing with it under stringent conditions wherein the nucleic acid sequence or a recombinant vector containing this sequence is introduced into a suitable host cell, the host cell is cultured under conditions in which an expression of the nucleic acid sequence takes place and the protein is isolated from the cell or cell supernatant. Stringent hybridization conditions are preferably defined according to Sambrook et al. (1989) Molecular Cloning A Laboratory Manual, Second Edition, Cold Spring Harbor Laboratory Press, and comprise a wash step of 30 min in 0.1×SSC, 0.5% SDS at 68° C.

The VLP according to the invention can furthermore have one or several additional heterologous proteins in the capsid structure. This means that a heterologous protein is anchored in the capsid structure, at least part of this protein being preferably accessible from outside. In principle all proteins are suitable as this heterologous protein which can be incorporated into the capsid structure and do not impair the self-assembly of the VLP. For example it may be desirable to provide the VLP with an antigenic determinant by means of the heterologous protein that can be detected by a specific antibody. On the other hand the heterologous protein can be a binding partner for a cell surface receptor which enables an interaction of the VLP with a specific class or subclass of cells which carry the corresponding receptor. After binding to the receptor such an interaction is for example the triggering of a particular signal or the internalization of the VLP.

The origin of the proteins is not limited to a particular organism and, depending on the special type of application, it is possible to incorporate eukaryotic, in particular human proteins, and also prokaryotic or viral proteins into the VLP. Examples of suitable proteins are surface proteins or membrane proteins, explicit examples of which are CD4 for a human cell surface receptor and the envelope protein of an immuno-deficiency virus e.g. HIV-gp 120 for a viral surface protein. It goes without saying that the heterologous protein can be modified if necessary, e.g. shortened, using recombinant methods especially if the natural protein cannot be incorporated into the VLP or impairs the self-assembly.

In a further special embodiment the VLP can contain one or several active substances inside the capsid structure. In this description an active substance is understood as any molecule which is not usually present in the medium used for self-assembly. Such active substances include for example macromolecules such as nucleic acids i.e. RNA, DNA or artificial modified nucleic acids as well as proteins and other physiologically active substances that can be of a natural, synthetic or recombinant type. Examples of such physiologically active substances are e.g. lipids, phospholipids, peptides, drugs, toxins etc.

Yet a further subject matter of the present invention is a nucleic acid which codes for a VP1 protein and comprises (a) the nucleotide sequence shown in SEQ ID NO. 1
(b) a nucleotide sequence corresponding to the sequence from (a) within the scope of the degeneracy of the genetic code or/and
(c) a nucleotide sequence hybridizing with one of the sequences from (a) or/and (b) under stringent conditions.

The nucleic acid according to the invention is preferably located on a recombinant vector, in particular under the control of an expression signal. Examples of suitable vectors are described in Sambrook et al., Supra, chapters 1, 2, 3, 4, 16 and 17. The invention also concerns a cell which is transformed with a vector according to the invention.

A further aspect of the invention also concerns a process for the production of a VLP in which VP1 is purified and converted into a form in which an assembly of several VP1 molecules to form a VLP takes place. Suitable conditions for assembly are for example present when VP1 is purified from a cell culture supernatant after a differential cushion centrifugation over sucrose and metrizamide.

The VLP is preferably produced recombinantly in which case a nucleic acid coding for a VP1 protein is introduced into a cell, the transformed cell is cultured in a medium under conditions in which an expression of the nucleic acid takes place and the expression product is isolated from the cell or from the medium. The recombinant VP1 is isolated directly from the host cells or/and the cell culture supernatant depending on the host/vector system used.

The advantage of the recombinant process is above all that VLP can be obtained in a simple manner, in high purity and in large amounts. The use of baculoviruses together with insect cells, e.g. with the insect cell line Sf 158, has proven to be an effective expression system in practice.

In order to produce VLP which have incorporated a heterologous protein within the capsid structure or VLP which contain an active substance inside the capsid structure, the above-mentioned production process is modified by adding the heterologous proteins or/and active substances in the desired amount or concentration at a suitable time point i.e. before assembly of the VLP and subsequently allowing the assembly. In this manner VLP can form which have incorporated a heterologous protein into the capsid envelope or/and contain an enclosed active substance, e.g. a nucleic acid, inside. Heterologous polypeptides can for example be incorporated into the capsid envelope by recombinant co-expression of the respective polypeptides i.e. of the VP1 polypeptide and of the heterologous polypeptide in a suitable host cell e.g. a eukaryotic cell. Active substances can be incorporated into the interior of the capsid envelope by for example dissociation of the capsid envelope and subsequent re-association in the presence of the active substance or by osmotic shock of the VLP in the presence of the active substance.

Yet a further aspect of the present invention concerns a method for the immunological determination of specific antibodies to JCV in a sample in which the antibodies are detected qualitatively or/and quantitatively by binding to a VLP composed of VP1 or to a component thereof. For reasons of ready availability it is preferable to use VLP composed of recombinant VP1 molecules.

A large number of test formats for such immunological methods of determination are known to a person skilled in the art and therefore do not have to be individually elucidated. In general such methods are carried out by contacting the VLP or components thereof with the sample under suitable conditions in order to allow binding of specific antibodies against the JC virus to the VLP or components thereof, separating the immune complexes formed from other sample components and detecting the presence of antibodies. For this one can for example use VLP which are adsorptively or covalently coupled to a solid phase or coupled via a suitable binding partner.

The antibody to be detected that is bound to the virus protein after incubation with the sample liquid is subsequently detected by a specific receptor directed against the antibody to be detected e.g. a detection antibody, protein A or an antigen capable of binding to the antibody e.g. a VLP. The exact type of this receptor is not critical and it is for example possible to use polyclonal or monoclonal detection antibodies such as anti-human antibodies from various animal species such as rabbits, mice or goats or antibodies that are specifically directed against the Fc part of immunoglobulins or immunoglobulin classes.

The receptor capable of binding to the antibody to be detected additionally includes an agent that allows the detection i.e. a label that is directly or indirectly associated with the receptor e.g. by means of specific binding pairs such as biotin/avidin. Such labels are also known to a person skilled in the art and for example include radioactivity, enzymes, luminescent or fluorescent labels. A particularly preferred test format is the ELISA in which a receptor with an enzyme label is used.

The above-mentioned immunological method of determination can be used to diagnose progressive multifocal leukoencephalopathy (PML) if cerebrospinal fluid (CSF) is used as the sample. In a preferred embodiment a parallel determination is carried out to diagnose PML in which CSF and serum from the same person are used as samples, both these samples being preferably collected in parallel. In order to obtain well-founded results it is particularly preferable to standardize the measured values relative to the total immunoglobulin concentration. A suitable reference parameter is the so-called antibody specificity index (ASI) which is defined as the ratio of the titre of specific antibodies to JCV in CSF and serum divided by the ratio of the Ig total concentration in CSF and serum. It has turned out that an ASI value of $\geq 1.5$ for a positive diagnosis of PML gives reliable results.

Hence a further subject matter of the present invention is a test kit for the determination of specific antibodies to JCV which comprises, in a separate spatial arrangement, VLP of JCV or components thereof, an agent for the detection of antibodies and optionally conventional buffers and auxiliary substances. The test kit is preferably suitable for the detection of human antibodies. The agent for the detection of antibodies includes in particular a receptor capable of binding specifically to the antibody to be detected which is provided directly or indirectly with a detectable label. The test kit can also contain the necessary substrates and detection substances.

The VLP according to the invention can also be used therapeutically e.g. for the treatment of PML. Hence the VLP according to the invention are suitable for the production of a therapeutic or/and prophylactic vaccine which is used against an infection with JCV. In this regard a VLP should be used in particular which neither contains heterologous proteins incorporated into the capsid structure nor encloses active substances inside. By this means it is possible, on the one hand, to saturate receptors on the surface of the oligodendrocytes in order to at least slow down further infection and, on the other hand, to stimulate the humoral immune response to JCV. The cellular immune response which can be detected by an antigen-specific T cell proliferation can also be stimulated by administering recombinant VP1. However, modified VLP can also be used alternatively which then have preferably incorporated a binding partner for a surface receptor of the corresponding target cells, i.e. in particular of oligodendrocytes, into the capsid structure and have enclosed at least one active substance in the interior which prevents the multiplication or spreading of the virus. In this case the active substance is preferably a virostatic agent such as cytosine arabinoside.

In a further embodiment the VLP can be used as a transport vehicle. Such VLP contain a suitable active substance enclosed in their interior and preferably a heterologous protein incorporated into the capsid structure which is capable of binding to a specific surface receptor of the desired target cell. This ensures the specificity of the interaction with the intended target cells and can be adapted to numerous cell types depending on the use. An example of such a use is the site-directed transport of TNF-α antisense nucleic acids to oligodendrocytes in multiple sclerosis since it is known that in this disease a surge of TNF-α expression leads to demyelinization. Another example is the use of VLP as a transporter system for nucleic acids in gene therapy.

Therefore a further subject matter of the invention is a pharmaceutical composition comprising a VLP as well as optionally conventional buffers, auxiliary agents, additives or/and diluents. The VLP in this case can be an unmodified VLP or a VLP with a heterologous protein incorporated into the capsid structure or/and with an active substance enclosed in the interior.

The invention is now further elucidated by the following examples as well as by the attached figures and sequence protocols.

| | |
|---|---|
| SEQ ID NO. 1 | shows the nucleotide sequence of a DNA sequence isolated from JCV which codes for VP1; |
| SEQ ID NO. 2 | shows the corresponding amino acid sequence; |
| SEQ ID NO. 3 | shows an amplification primer used to isolate the VP1 coding sequence; |
| SEQ ID NO. 4 | shows a further amplification primer and |
| Brief Description of Drawings: | |
| FIG. 1 | shows a schematic representation of the working steps to prepare recombinant VP1; |
| FIG. 2 | shows the packaging of heterologous DNA in VP1-VLP, |
| FIG. 3 (Parts A–E) | shows the immunoreactivity of an anti-VP1-VLP immune serum and |
| FIG. 4 | shows the neutralization of JCV by an anti-VP1-VLP immune serum. |

EXAMPLES

Example 1

Recombinant production of JCV-VP1

JCV-DNA (strain Mad-4) was isolated from SVG cells and the sequence coding for the VP1 gene was amplified by means of PCR. The following primers were used for the PCR which were provided with a BamHI and HindIII restriction cleavage site for the subsequent cloning.

```
Primer 1 (SEQ ID NO. 3):

5'-GTA CGG GAC TGC AGC ACC TGC TCT TGA AG-3'

Primer 2 (SEQ ID NO. 4):

5'-TAC AAT AAA AGC TTT TGA TTA CAG CAT TT-3'
```

In the PCR reaction 100 pmol of each primer was used in a reaction volume of 50 μl. The DNA was preamplified in a 50 μl mixture by 20 amplification cycles comprising 45 s denaturation at 94° C., 45 s annealing at 55° C. and 45 s extension at 70° C. The denaturation was extended to 5 min in the first cycle. Each subsequent extension was increased by 1 s and the last cycle was extended to 5 min. 10 μl of this reaction was mixed with the primers and 2.0 U Taq DNA polymerase (Pharmacia, Freiburg, Germany) and subjected to a PCR under the above conditions for a total of 25 cycles.

The PCR products were purified by agarose gel electrophoresis, cleaved with BamHI and HindIII and ligated into the cloning site of a BamHI/HindIII cleaved p-BlueBac-III vector (Invitrogen, Netherlands) to obtain the vector pBlueBac-VP containing the VP1 gene. After transformation of *E.coli* cells with pBlueBac-VP and identification of positive clones, the recombinant plasmids were isolated and transfected into Sf 158 insect cells with wild-type baculovirus DNA.

After passaging the supernatant twice on Sf 158 cells, the recombinant baculoviruses were purified (cf. FIG. 1).

The recombinant VP1 was expressed in the Sf 158 host cells and secreted into the cell supernatant at a concentration of 0.9 mg protein per ml. The expression was detected by Western blot of cell culture supernatants using a rabbit anti-SV40 hyperimmune serum.

It was possible to purify the VP1 to homogeneity from the cell culture supernatant by means of differential cushion centrifugation over sucrose and metrizamide.

It can be shown by electron microscopic investigations that the VP1 associated to form VLP that have an icosahedral structure with a diameter of about 50 nm and a density of ca. 1.31 g/ml in CsCl gradients. Protein biochemical investigations of the VP1 contained in the VLP by means of mass spectroscopy after tryptic digestion yielded the expected fragment masses. The recombinant VLP proved to be highly immunogenic after immunization in rabbits.

Example 2

Immunological Determination of Specific Antibodies to the JC Virus in Serum and CSF Recombinant VP1 was titrated out against the hyperimmune serum to SV40 from rabbits and antisera of PML patients. The optimal antigen concentration was determined as 200 ng protein of the product obtained after differential cushion centrifugation corresponding to ~70 ng VP1 per well. CSF total protein was determined by means of trichloroacetic acid precipitation. Immunoglobulin G and albumin in the serum and CSF were determined immunochemically by nephelometry. Intrathecal antibody synthesis was analysed according to the methods of Reiber and Lange (Clin. Chem. 37 (1991), 1153–1160) and Weber et al., (J. Immunol. Methods 136 (1991), 133–137). Intrathecal synthesis of VP1-specific antibodies was defined as a ratio of the antibody titre in CSF and serum (ASI) of at least 1.5.

In order to carry out the determination 200 ng of the cell culture supernatant of Sf 158 cells infected with pBlueBac-III-VP1 was applied to each well of a microtitre plate with 96 wells (Grainer Frickenhausen, Germany) at 4° C. for 12 to 14 hours. The unspecific binding was saturated by incubation for 1 hour at 37° C. with 200 μl 5% Blotto per well. Serum was diluted in Blotto starting at 1:500 in log2 steps and the highest dilution used was 1:80,000. CSF was diluted in Blotto starting at 1:5 in log2 steps and the highest dilution used was 1 to 40,000. After binding the primary antibody for 3 hours at 37° C., the plates were washed seven times with 150 mM PBS containing 0.05% Tween 20. Bound antibody was detected by incubation for 2 hours at 37° C. with a peroxidase-conjugated anti-human IgG antiserum from rabbits (Jackson Laboratories Dianova, Hamburg, Germany).

After washing seven times with PBS, the peroxidase-conjugated antibody was visualized using o-phenylenediamine. After 15 minutes the reaction was stopped with 1.3 N sulfuric acid and the optical density (OD) was measured at 495/620 nm in a Titertek MC340 MKII-ELISA reader. The antibody titre in CSF and serum was calculated using EXEL™.

In selected cases a Western blot analysis of the intrathecal immune response was carried out. After electrophoretic separation of 1 μg VP1 per lane in a 12% SDS-PAGE gel, the antigen was transferred electrophoretically onto a HiBond-PVDF membrane (Amersham Buchler KG, Germany). The unspecific antibody binding was saturated for 1 hour at 37° C. with 5% Blotto. Serum or CSF antibodies were added to each lane at an IgG concentration of 10 mg/l and incubated for 3 hours at 37° C. After three washes in PBS the membranes were incubated with a peroxidase-conjugated anti-human IgG antiserum from rabbits (Jackson Laboratories Dianova, Hamburg). Bound detection antibodies were visualized according to the manufacturer's instructions on Hyperfilm-ECL using an ECL kit (Amersham Buchler KG, Germany).

Example 3
Diagnostic Determination of PML

Parallel CSF/serum samples from 189 patients were examined. Intrathecal synthesis of anti-VP1 antibodies was found in 28/34 (82%) of the PML patients at an ASI ≧1.5 whereas an ASI ≧1.5 was only found in 5/155 of the control patients. Serum antibodies to VP1 were found in all PML patients as well as in 28/37 (76%) of the multiple sclerosis patients, 43/50 (86%) of the control group, 29/33 (88%) of patients with impaired blood-brain barrier function and 31/35 (89%) of the HIV-positive patients.

The intrathecal synthesis of anti-VP1 antibodies was checked by Western blot analysis in individual cases. An almost identical intensity in the CSF and serum was obtained in PML patients with a VP1 ASI <1.5 whereas 4 sera from patients with ASI in the range 12–107 exhibited very weak serum bands and considerably stronger CSF bands.

A statistical analysis of the antibody specificity indices (ASI) was carried out in the 5 different patient groups. In the normal group the average VP1 ASI was 0.92 (±0.16, range 0.65–1.26), in the multiple sclerosis groups it was 0.91 (±0.38, range 0.34–2.49), in the group with impaired blood-brain barrier function it was 0.92 (±0.22, range 0.52–1.36), in the HIV-positive group it was 4.35 (±12.7, range 0.35–67.2) and in the PML group it was 12.59 (±24.42, range 0.38–107). Using the Kruskal-Wallis test a significant difference is found between the 5 groups (P<0.0001). Using the Mann-Whitney test there is a significant difference between the PML group and the control group, the group with impaired blood-brain barrier function and the multiple sclerosis group (P<0.0001) and between the PML group and the HIV-positive group at P<0.001. The differences between the other 6 group pairs were not significant.

The above results show that an examination of the intrathecal synthesis of antibodies directed against JCV-VP1 is a suitable test for the diagnosis of PML. In the investigation carried out a sensitivity of 82% and a specificity of 96% was found using a statistically significant VP1-ASI of ≧1.5. Although the ELISA assay thus has a somewhat lower sensitivity than a PCR assay with nested primers (93%) it represents a useful addition to current test procedures since it is more cost-effective, simpler to carry out and less susceptible to false-positive results by contamination. Important applications include the screening and examinations of numerous samples, the rapid determination of unequivocally positive samples as well as the exclusion of unequivocally negative samples since according to the present results a negative antibody test in serum excludes the diagnosis of PML.

Example 4
Detection of a Cellular Immune Response to Recombinant VP1

It was possible to detect a cellular immune response to recombinant JCV-VP1 in a healthy test person and a PML patient. The antigen-specific proliferation was dose-dependent. An antigen-specific T cell proliferation was detected at a final concentration of 1–10 μg antigen which reached its maximum on the 6th day. This experiment indicates that healthy test persons and PML patients also have a cellular immune response to JCV and in particular to the VP1 protein in addition to a humoral response.

Example 5
Packaging of foreign proteins and exogenous DNA in VLP of the main structural protein VP1 of JCV
5.1 Packaging of viral envelope glycoproteins In order to package a foreign protein VP1 and the envelope glycoprotein gp160 of the ape immunodeficiency virus SIVmac32H were co-expressed in a model experiment. In both cases the vector pBlueBac already mentioned in example 1 was used as the base vector for the expression.

For this Sf158 cells were infected at a multiplicity (number of infectious units per cell) of 5 with the baculoviruses recombinant for VP1 and at a multiplicity ratio of gp160 to VP1 of 0.2, 0.5 and 2. Five days after the co-infection the cells and the cell culture supernatants were examined by Western blot analysis for the presence of gp160 and VP1. In this examination it was possible to detect the efficient coexpression of gp160 and VP1 with an antibody mixture directed against gp160 and VP1. It was also possible to detect gp160 and VP1 separately. In this case a multiplicity ratio of 2 yielded the best coexpression result. The association of gp160 with the VP1-VLP was demonstrated after pelleting the cell culture supernatant through a 40% sucrose cushion. It was possible to detect gp160 separately in the resulting pellet as well as gp160 and VP1 by means of the antibody mixture.

5.2. Packaging of exogenous DNA

Within the framework of developing efficient transfer systems for gene therapy it was examined whether exogenous DNA can be packaged into the VP1-VLP. Three approaches were investigated for this. The purified VP1-VLP were suspended in TBS/Ca (10 mM Tris-HCl pH: 7.5, 150 mM NaCl, 0.01 mM $CaCl_2$), $H_2O$ redistilled or dissociation buffer (TBS pH: 8.5 containing 10 mM EGTA and 5 mM DTT). Exogenous DNA in the form of a pUC18 derivative which carries the 1.2 kB long V1/V2 region of the env gene for the envelope glycoprotein of HIV-1han2 whose sequence has been published by Sauermann et al. (AIDS Research and Human Retroviruses 6 (1990), 813–823) (total vector ca. 4.1 kB) was added at a weight ratio of DNA to VP1-VLP of 1:10 and 1:20. The incubation was carried out for 60 minutes at 37° C. The reaction mixture carried out in TBS/Ca was then subjected to an osmotic shock and incubated for a further 30 minutes at 37° C. All samples were then dialysed overnight against reassociation buffer (TBS pH: 7.5 containing 1 mM $CaCl_2$). Subsequently all samples were digested intensively with DNase I, diluted with TBS/Ca and ultracentrifuged overnight through a 40% sucrose cushion. After resuspension of the particles, the DNA was extracted and the V1/V2 region (ca. 1.8 kB) was amplified by PCR by means of specific primers and the amplificate was separated in an agarose gel. In this experiment it was found that exogenous DNA could be packaged into the VP1-VLP (FIG. 2) using all three methods (lanes 1 to 6). The exogenous DNA was efficiently protected against digestion with DNase I after packaging. The best packaging efficiency was reached at a DNA to VP1-VLP ratio of 1:20 and after a sequence of dissociation and reassociation (lane 6).

According to an estimate based on the positive control it was possible to package about 3 to 4 g exogenous DNA into 80 g purified VP1-VLP.

Example 6
Development of a Therapeutic Vaccine Against the Human Polvomavirus JCV Based on VLP of the Main Structural Protein VP1

In order to produce a therapeutic vaccine against the human polyomavirus JCV the main structural protein VP1 was expressed in insect cells with the aid of recombinant baculoviruses (example 1). After expression VP1 forms typical virus-like particles (VLP). The VLP represent a mixture of empty and full particles with a diameter of about 50 to 60 nm. The VP1-VLP were purified to homogeneity and exhibited a floating density in CsCl gradients of 1.32 g/ml (empty particle) and 1.34 g/ml (full particle).

Immunogenicity of VP1-VLP

Figure 3A:
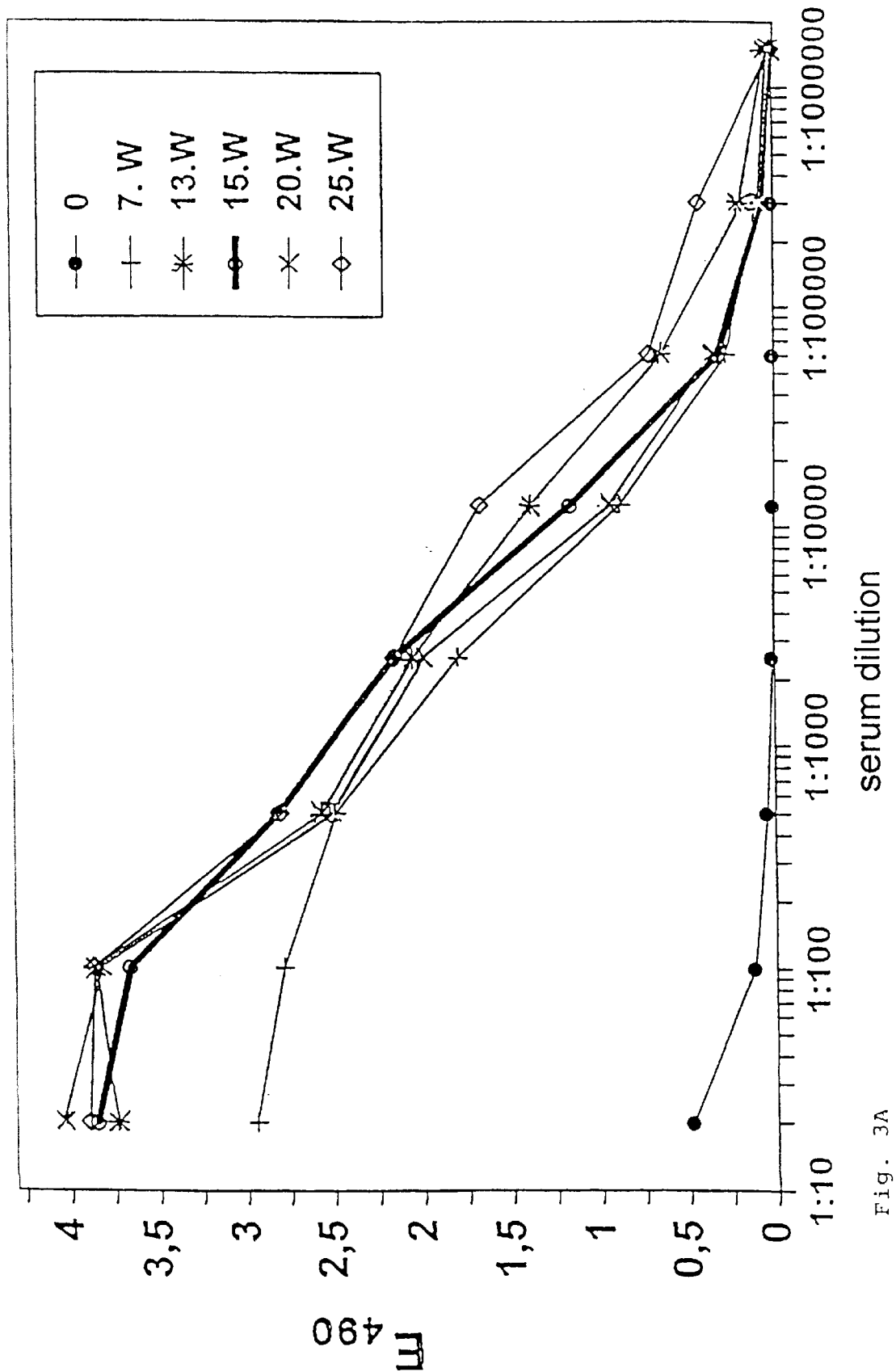

In order to examine the immunogenicity 100 µg of the purified VP1-VLP were mixed with 300 µg haemocyanine from the keyhole limpet, emulsified in complete Freund's adjuvant and a rabbit was intramuscularly immunized therewith. A booster immunization was carried out four weeks later with incomplete Freund's adjuvant. The analysis of the titre of anti-VP1 antiserum in an ELISA at various collection dates after the last immunization of the rabbit is shown in FIG. 3A. 50 ng of the purified VP1-VLP was absorbed to an ELISA plate (Greiner, Nurtingen) for the investigations and the anti-VP1 antiserum of the corresponding collection dates (+: 7 weeks; *: 13 weeks, □: 15 weeks; X: 20 weeks; ◊: 25 weeks) were titrated out at the stated dilutions. The end point titre was defined as the dilution at which the reactivity corresponded to that of the preimmunization serum (−). As can be seen in FIG. 3A the immune serum had reached an end point titre of about $10^5$ six weeks after the last immunization.

Figures 3B, 3C, 3D, 3E:
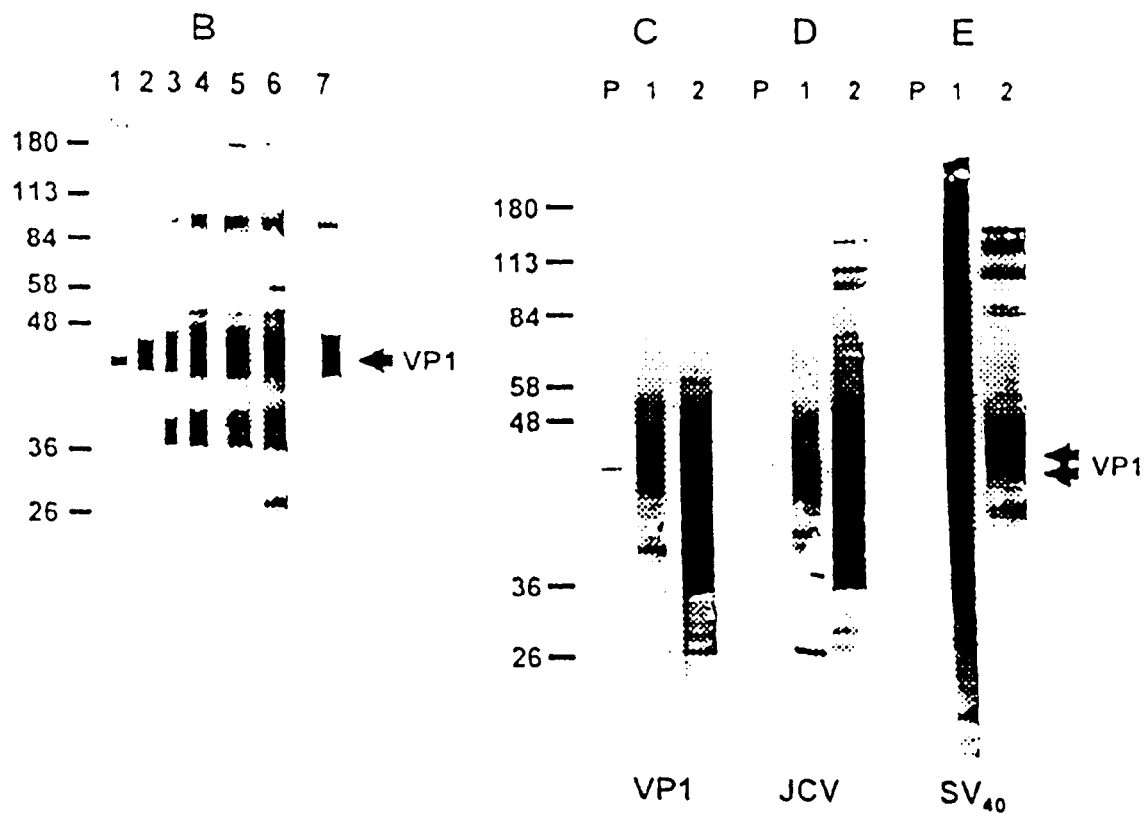

The specificity of the anti-VP1 antiserum was examined in a Western blot (WB). For this about 20 ng purified antigen per lane was separated by means of SDS polyacrylamide gel electrophoresis and transferred onto a nitrocellulose membrane. In FIG. 3B the VPS1-VLP were used as the antigen and the reactivity of the anti-VP1 antiserum from various collection dates (lane 2: 7 weeks; lane 3: 13 weeks; lane 4: 15 weeks; lane 5: 20 weeks; lane 6: 25 weeks) was compared with the reactivity of a preimmunization serum (lane 1) and with an anti-SV40 hyperimmune serum (lane 7). In FIG. 3C purified VP1-VLP were also used whereas in FIG. 3B purified natural JCV particles and in FIG. 3E purified natural SV40 particles were used as the antigen. In figures C–E each lane P represents the preimmunization serum, each lane 1 represents the anti-SV40 immune serum and each lane 2 represents the anti-VPS antiserum.

The specificity of the antiserum was as expected. As shown by a Western blot analysis only VP1-VLP-specific proteins were recognized and a considerable increase of the reactivity depending on the bleeding time point after the last immunization was observed (FIG. 3B, lanes 2 to 6). The reactivity was comparable with an anti-SV40 hyperimmune serum (lane 7). The immunoreactivity of the anti-VP1-VLP immune serum was also tested against various antigens. The hyperimmune serum additionally recognized the VP1 of SV40 (FIG. 3D, lane 1) and the VP1 of natural JCV (FIG. 3E, lane 1) in addition to the recombinant VP1 (FIG. 3C, lane 1). Again the reactivity was comparable with that of the anti-SV40 immune serum (FIGS. 3C to E, lane 2 in each case).

Binding and Inhibition of the Binding of the VP1-VLP to SVG Cells

For these experiments the VP1-VLP were labelled with $^{125}$I. Firstly the ratio of the $^{125}$I-VP1-VLP and SVG cells was determined which were obtained by transfection of human foetal glial cells with a SV40 mutant with a defect in the replication of origin (Major et al., Proc. Natl. Acad. Sci. USA 82 (1985), 1257–1261). A saturation binding was achieved with $2 \times 10^6$ cpm $^{125}$I-VP1-VLP and $10^5$ SVG cells. The binding inhibition of the anti-VP1-VLP immune serum was examined under these test conditions. The $^{125}$I-VP1-VLP binding was suppressed by 95% at serum dilutions of 1:5 and 1:10 and a binding inhibition of about 75% was still observed even at a serum dilution of 1:20. Whereas a binding inhibition of only 20% was measurable at a serum dilution of 1:40, no binding inhibition was achieved at a serum dilution of 1:80.

Neutralization of JCV

Figure 4:
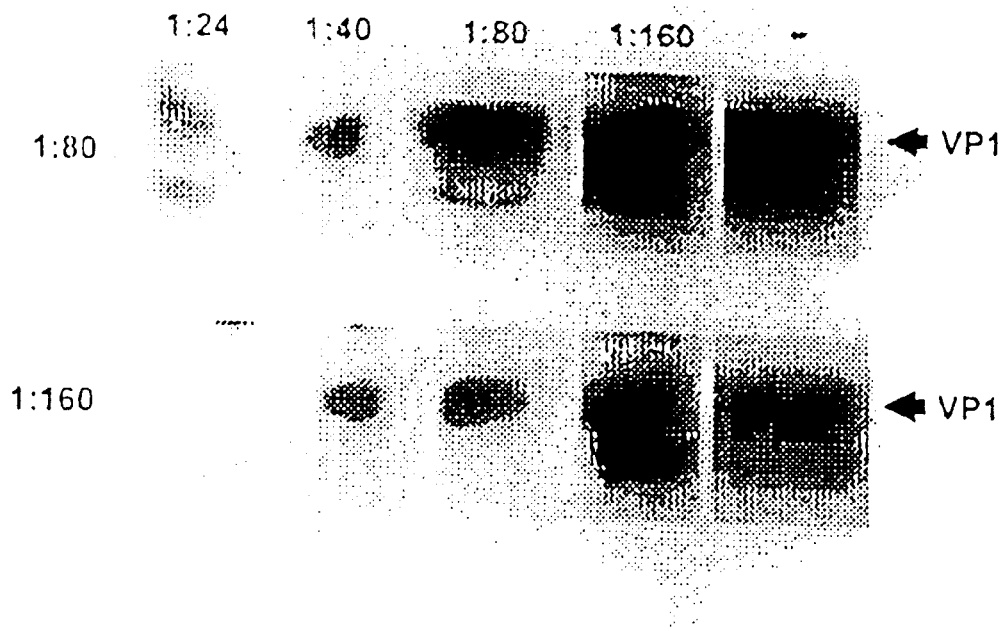

A new test was developed to examine the neutralization capacity of the VP1-VLP hyperimmune serum. This test is based on the intracellular detection of VP1 after infection of SVG cells with JCV. As can be seen in FIG. 4 a complete neutralization of JCV was achieved at a dilution of the JCV infection stock of 1:160 and a serum dilution of 1:24 since no VP1 was detectable. At a serum dilution of 1:40 VP1 was recognized but in a reduced form which indicates a partial JCV neutralization. This also applies to a serum dilution of 1:80, whereas at a serum dilution of 1:160 no neutralization effects were achieved in comparison to a control. Similar results were also obtained at a dilution of the JCV infection stock of 1:80.

These results show that the VP1-VLP induce the immune response which would be expected of a vaccine with a potential for success. Neutralizing and binding inhibiting antibodies were induced. Moreover the VP1-VLP are also able to induce a proliferative T cell reactivity in the peripheral blood lymphocytes of JCV-positive but healthy individuals (examples 2–4).

What is claimed is:

1. A non-infectious virus-like particle, wherein said particle comprises several molecules of the virus protein VP1 of the JC virus as the only JCV component in the virus like particle.

2. The particle according to claim 1, wherein said VP1 is recombinant VP1.

3. The particle according to claim 1, wherein said VP1 is coded by a nucleic acid comprising
   (a) the nucleotide sequence shown in SEQ ID NO:1

(b) a nucleotide sequence which encodes the amino acid sequence according to SEQ ID NO:2, and (c) a nucleotide sequence hybridizing with one of the sequences from (a)–(b) under conditions that comprise a wash step of 30 minutes in 0.1×SSC, 0.5% SDS at 68 C.

4. The particle according to claim 1, wherein said particle has at least one additional heterologous protein incorporated into the capsid structure.

5. The particle according to claim 4, wherein the additional protein is a cell surface receptor or a binding partner for a cell surface receptor.

6. The particle according to claim 5, wherein the additional protein is a viral surface protein.

7. The particle according to claim 5, wherein the additional protein is gp120 from HIV.

8. The particle according to claim 1, wherein said particle contains at least one active substance inside the capsid structure.

9. The particle according to claim 8, wherein the active substance is selected from the group consisting of nucleic acids, proteins and physiologically active substances.

10. The particle according to claim 9, wherein the active substance comprises a nucleic acid.

11. A process for the production of a non-infectious virus-like particle, wherein said particle comprises several molecules of the virus protein VP1 of the JC virus as the only JCV component in the virus like particle, comprising purifying VP1, and assembling several VP1 molecules to form a non-infectious virus like particle.

12. The process according to claim 11, further comprising introducing a nucleic acid coding for a VP1 protein into a cell, culturing the transformed cell in a medium under conditions in which the nucleic acid is expressed, and isolating the expression product from the cell or from the medium.

13. The process according to claim 12, wherein said nucleic acid coding for a VP1 protein comprises (a) the nucleotide sequence shown in SEQ ID NO:1, (b) a nucleotide sequence encoding an amino acid sequence according to SEQ ID NO:2, and (c) a nucleotide sequence hybridizing with one of the sequences from (a)–(b) under conditions that comprise a wash step of 30 minutes in 0.1×SSC, 0.5% SDS at 68° C.

14. The process according to claim 12, wherein the nucleic acid coding for a VP1 protein is present in at least one copy on a recombinant vector.

15. The process according to claim 14, wherein the expression of said VP1 protein is under the control of an expression signal.

16. The process according to claim 12, wherein said cell is an insect cell.

17. The process according to claim 11, wherein the assembly is carried out in the presence of at least one additional protein during which the protein is incorporated into a non-infectious virus-like particle comprising more than one VP1 molecule.

18. The process according to claim 11, wherein the assembly is carried out in the presence of a further substance during which the substance is enclosed in a non-infectious virus-like particle comprising more than one VP1 molecule.

19. The process according to claim 18, wherein said further substance is a nucleic acid.

20. A method for the immunological determination of specific antibodies against JCV in a sample, comprising obtaining a sample from a patient, binding any antibodies in said sample to a non-infectious virus like particle or a component thereof, wherein said particle comprises several molecules of the virus protein VP1 of the JC virus as the only JCV component in the virus like particle, and detecting any antibody/VP1 complexes qualitatively, quantitatively or both qualitatively and quantitatively as an indication of said specific antibodies against JCV.

21. The method according to claim 20, wherein said virus protein VP1 is recombinant VP1.

22. The method according to claim 20, further comprising separating any formed immune complexes from other sample components, and detecting the presence of antibodies, wherein the virus like particles or components thereof are contacted with said sample under suitable conditions in order to allow binding of specific antibodies against JC virus to the virus like particles or to components thereof.

23. The method according to claim 20, wherein said sample is cerebrospinal fluid and said immunological method of determination is used to detect progressive multifocal leukoencephalopathy.

24. The method according to claim 23, further comprising carrying out a second determination using a serum sample from said patient, wherein said serum sample is collected from said patient at about the same time as said cerebrospinal fluid.

25. A test kit for the determination of specific antibodies against a JC virus, comprising a) a non-infectious virus-like particle, wherein said particle comprises several molecules of the virus protein VP1 of the JC virus as the only JCV component in the virus like particle, and b) an agent for the detection of antibodies.

26. The test kit according to claim 25, wherein said agent for the detection of antibodies comprises a specific receptor which binds to the antibodies to be detected and suitable detection agents.

* * * * *